United States Patent [19]

Fish

[11] Patent Number: 4,469,102
[45] Date of Patent: Sep. 4, 1984

[54] SUNTANNING BOOTH

[76] Inventor: Errol R. Fish, 590 N. 96th St., Mesa, Ariz. 85207

[21] Appl. No.: 219,916

[22] Filed: Dec. 24, 1980

[51] Int. Cl.³ .......................................... A61M 33/00
[52] U.S. Cl. ..................................... 128/395; 128/396; 128/371
[58] Field of Search ............... 128/371, 372, 395, 396, 128/362, 82.1

[56] References Cited

U.S. PATENT DOCUMENTS

| | | | |
|---|---|---|---|
| 1,583,420 | 5/1926 | Picard | 128/371 |
| 2,631,588 | 3/1953 | Paschell | 128/371 |
| 4,048,537 | 9/1977 | Blaisdell et al. | 313/489 |
| 4,100,415 | 7/1978 | Blaisdell et al. | 128/371 |
| 4,277,855 | 7/1981 | Poss | 128/371 |

OTHER PUBLICATIONS

"Oral Psoralen Photochemotherapy of Psoriasis", Fitzpatrick & Parrish, copy from Sylvania-GTE in Ex's Unofficial Digest, PUVA Lamps, R. E. Levin, Provided by Sylvania-GTE.
Eurotan International, Houston, Tex., brochure 1979.
Sontegra International Brochure, CPC Systems Inc., Mfg. and Distributor.
Euro Tan International Brochure Featuring "The Tanner Bed" & The Tanner Top, Houston, Tex. 1980.

Primary Examiner—C. Fred Rosenbaum
Assistant Examiner—C. W. Shedd
Attorney, Agent, or Firm—Cahill, Sutton & Thomas

[57] ABSTRACT

A suntanning booth rapidly tans an occupant by having a first source of radiant energy of a wave length of 320 to 400 nanometers and a second source of radiant energy of a wave length of 280 to 320 nanometers which simultaneously irradiate an occupant of the booth to stimulate secretion of melanin and to oxidize the melanin, respectively. Individual cooling systems for the radiant energy sources and the occupant are formed as part of the booth to maintain the temperatures of the radiant energy sources and the occupant at acceptable levels.

12 Claims, 6 Drawing Figures

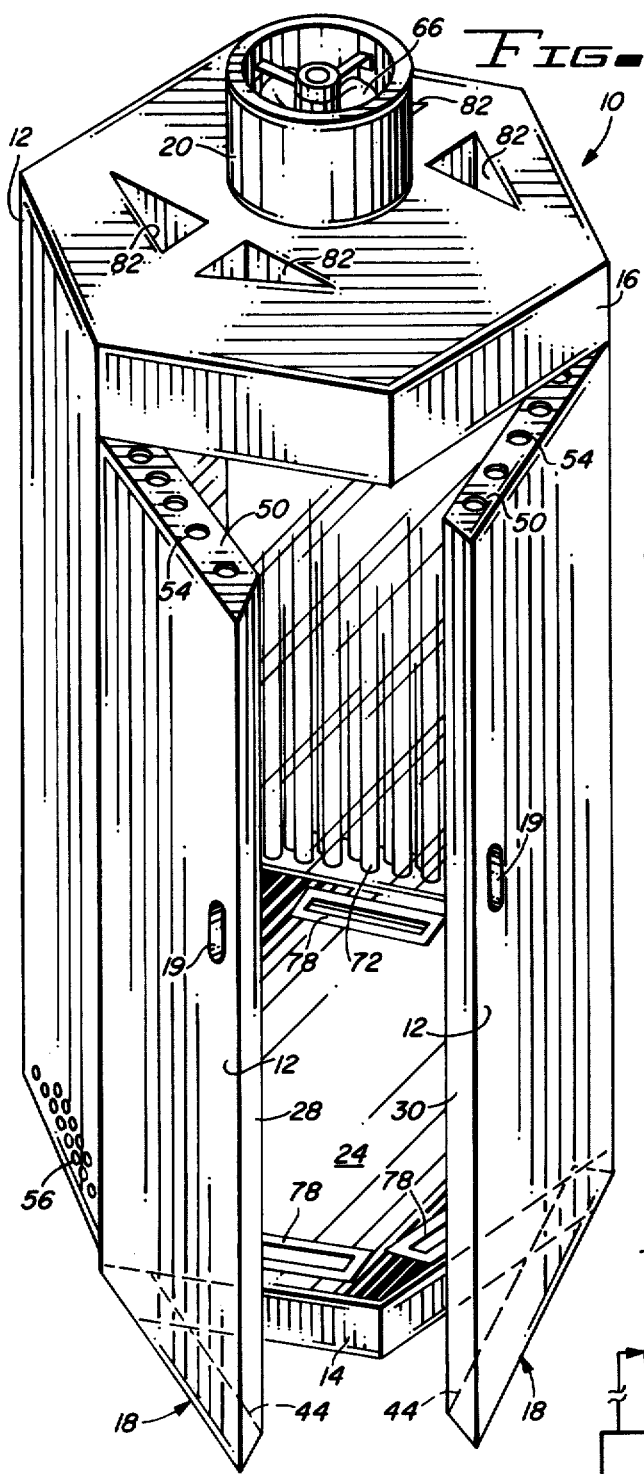
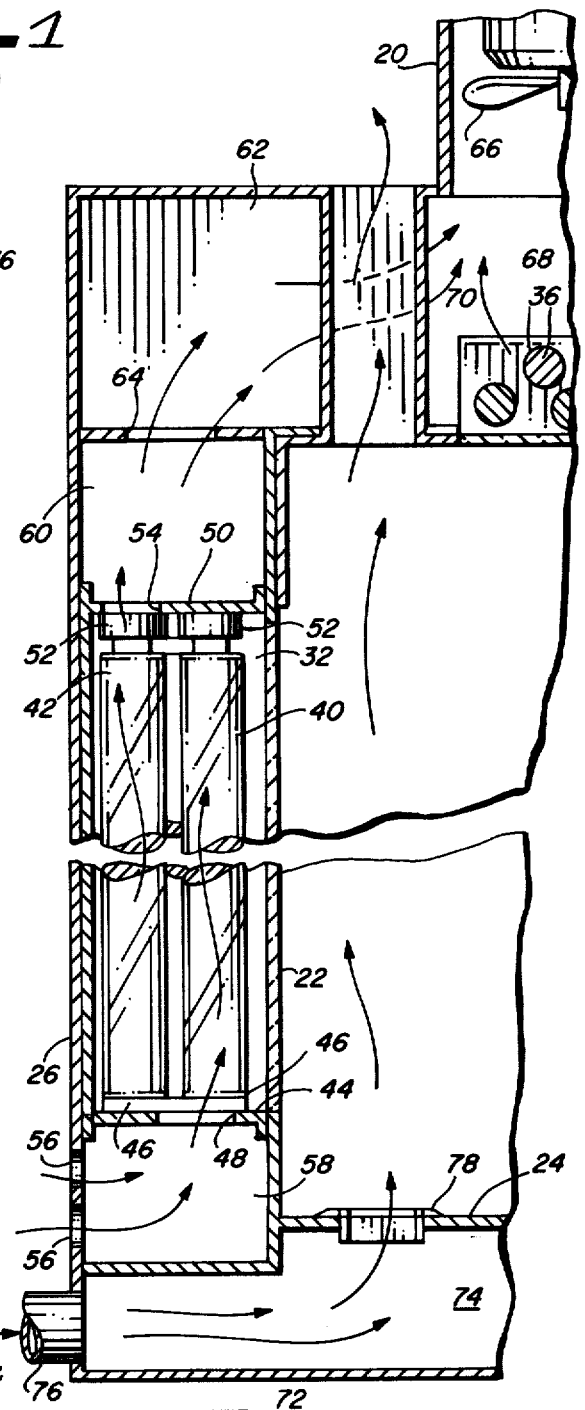
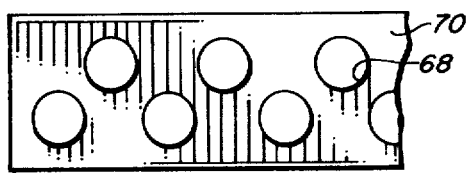
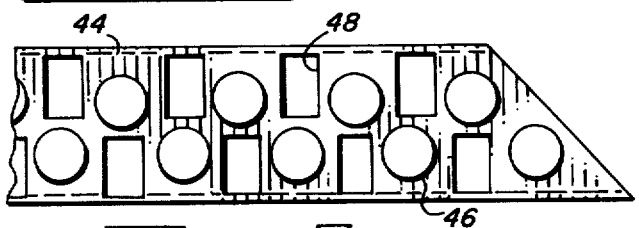

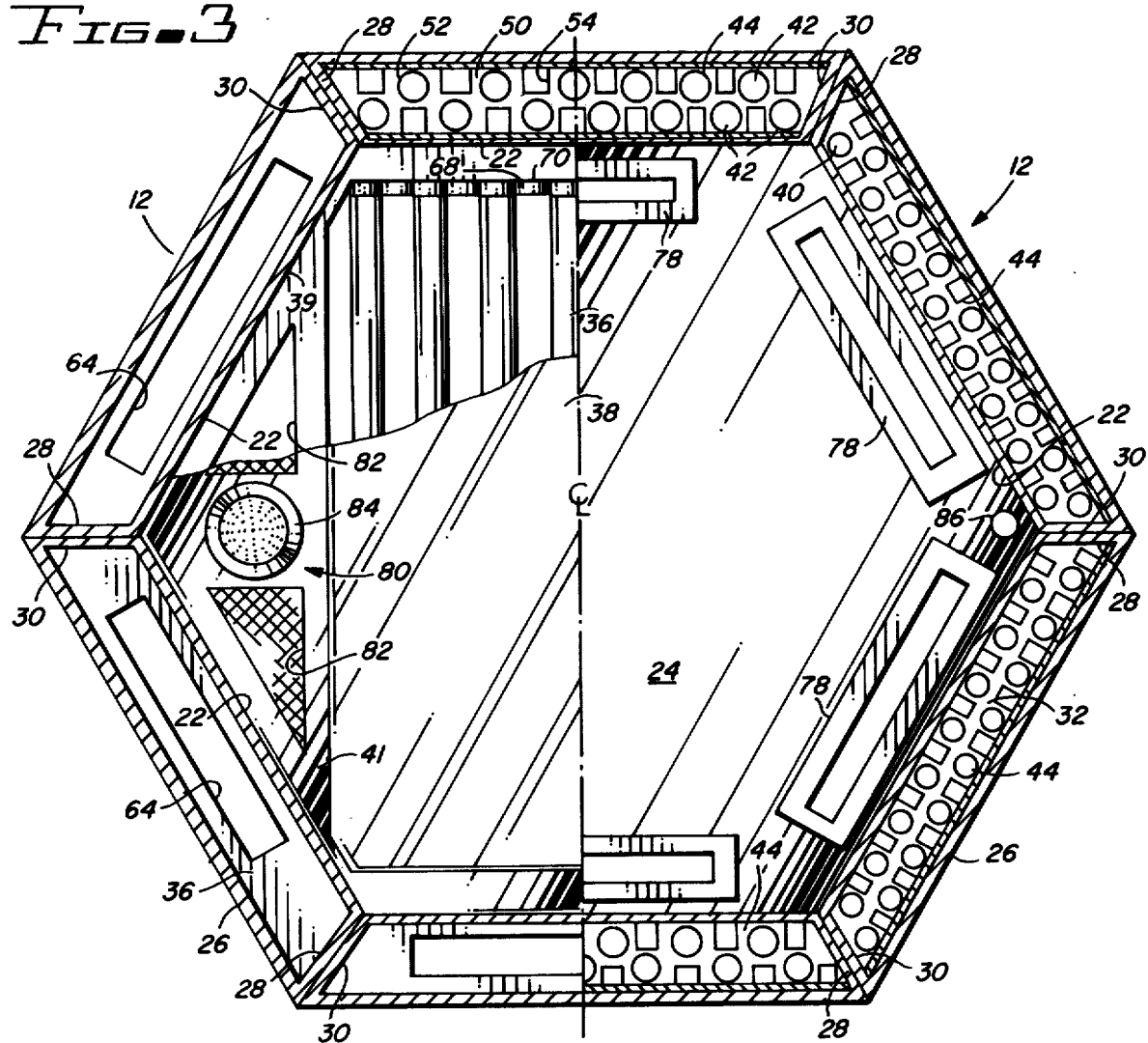

SUNTANNING BOOTH

The present invention relates to suntanning booths and, more particularly, to the source of the radiant energy used therein and to the cooling of the radiant energy source and the occupant.

The pursuit of an attractive suntan is universal. Millions of people irrespective of race expend a great deal of effort, time and money to obtain a tan, whether by natural or artificial irradiation.

With respect to artificial sources for producing a suntan or darkening an existing suntan, many devices have been developed. U.S. Pat. No. 2,493,328 is directed to a mobile solarium for irradiating an occupant with light from the sun. U.S. Pat. No. 2,631,588 describes a suntanning booth square in cross-section and having a source of radiant energy disposed adjacent one wall commensurate in height with the vertical portion of an occupant to be irradiated. U.S. Pat. No. Des. 248,315 depicts a configuration of a photochemotherapy chamber. U.S. Pat. No. 4,100,415 is directed to a standup booth hexagonal in cross-section which includes a single line of vertical ultraviolet light sources mounted in each panel; to achieve a tan an occupant is required to be injected with a drug compound known as psoralens to stimulate secretion of melanin, which melanin is subsequently oxidized by the ultraviolet light. U.S. Pat. No. Des. 248,968 illustrates a suntanning booth oval in cross-section and having an oval line of vertically oriented ultraviolet lights mounted therein. U.S. Pat. No. Des. 249,552 illustrates a suntanning booth octagonal in cross-section and having a line of vertically oriented ultraviolet lights mounted in each panel.

The tanning process of human beings is little understood but it is known that a complicated photobiological process sometimes referred to as photochemotherapy occurs. It is known that the skin contains cells called melanocytes, which cells secrete melanin, a granular appearing substance reddish brown in color. This is true of all races. Dark complected persons and negroes have a darker skin color because their melanocyte cells naturally continuously secrete more melanin than fair skinned persons and therefore their skin contains more pigmentation.

A suntan is achieved by oxidization of the secreted melanin which turns its reddish brown color to a dark brown or black. Thus, all persons, irrespective of their natural skin color will become tanned upon oxidization of the secreted melanin.

Secretion of melanin can be stimulated by subjecting the melanocyte cells to radiant energy having a wave length of 280 to 320 nanometers (hereinafter referred to as B wave lengths). Oxidization of the melanin occurs in the presence of radiant energy having a wave length of 320 to 400 nanometers (hereinafter referred to as a wave length). The radiant energy from the sun includes both A and B wave lengths of an intensity ratio of approximately one to six, respectively.

Radiant energy of an A wave length impinging upon the skin causes considerable discoloration of the skin due to oxidization of any existing melanin but without any noticeable reddening or other symptom associated with a sunburn. Radiant energy of predominately a B wave length produces little noticeable discoloration of the skin by oxidization of the melanin but it does produce substantial reddening of the skin, cooking of the skin until the outer layer dies and then peeling; a sunburn.

Ideally, a suntan booth should subject an occupant to irradiation of B wave length radiant energy of sufficiently high intensity—time ratio to stimulate secretion of the melanin but of sufficiently low intensity—time ratio not to cause any reddening of the skin. And, the person should be irradiated with A wave length radiant energy of sufficient intensity—time ratio to cause rapid oxidization of the secreted melanin. Thereby, a suntan can be achieved in a relatively short period. Preferably, irradiation of A and B wave length radiant energy should be simultaneous and the intensity ratio between the A and B wave length radiant energy should be one thousand to one. With this ratio, even the fairest complected person would not be sunburned and yet achieve a tan relatively quickly.

The vast majority of suntan booths presently in use employ sources of radiant energy which radiate radiant energy primarily of the B wave length. A sunburn can occur in such booths in as little time as two minutes. These booths are quite popular as secretion of melanin is well stimulated by B wave length radiant energy and discoloration of the skin due to the reddish brown color of the melanin will occur in a relatively short time. However the discoloration is not what would be generally called a good tan.

Subjecting a person to A wave length radiant energy only will cause some stimulation of the melanocytes to secrete melanin but the stimulation and secretion is approximately one thousand times less than that by the B wave length radiant energy. Therefore, a suntanning booth which employs a source of A wave length radiant energy causes no sunburning and does produce a suntan but the process is painstakingly slow and boring. However, the tan that finally results is considered very attractive.

The present invention is directed to a suntanning booth having an arrangement of a sufficient source of B wave length radiant energy to stimulate secretion a melanin but which is of insufficient intensity to cause reddening of the skin and sunburning and an arrangement of a source of A wave length radiant energy to maximize the intensity thereof to oxidize rapidly the secreted melanin. Moreover, a cooling air flow vent system is employed to maintain the sources of radiant energy within their operating temperature range and to maintain the occupant of the booth in a comfortable temperature range and minimize discomfort and fatigue.

It is therefore a primary object of the present invention to provide a suntanning booth which will rapidly produce a suntan without an accompanying sunburn.

Another object of the present invention is to provide a suntanning booth which will produce an attractive tan after a small number of exposure sessions of limited duration.

Still another object of the present invention is to provide a suntanning booth having a preferred intensity ratio of A and B wave length radiant energy.

Yet another object of the present invention is to provide an arrangement of sources for A wave length radiant energy which maximizes the intensity of the radiation.

A further object of the present invention is to provide physical segregation between an occupant and the sources of radiant energy located within a suntanning booth.

A still further object of the present invention is to provide separate air cooling systems within a suntanning booth for the occupant and for the sources of radiant energy.

A yet further object of the present invention is to provide a suntanning booth which has an economical ratio between cost and duration of use to achieve a good suntan.

These and other objects of the present invention will become apparent to those skilled in the art as the description thereof proceeds.

The present invention may be described with greater specificity and clarity with reference to the following drawings, in which:

FIG. 1 is an isometric view of the suntanning booth;

FIG. 2 is a partial cross-sectional view illustrating the air flow of the cooling systems;

FIG. 3 is a split interior view of the top and bottom of the booth;

FIG. 4 is a bottom view illustrating a door configuration;

FIG. 5 illustrates a baffle supporting the radiant energy sources located in the panels; and FIG. 6 illustrates a support member for the ceiling mounted radiant energy sources.

Referring to FIG. 1, there is shown a suntanning booth 10 which incorporates the principles of the present invention. The booth includes six panels 12 detachably attachable to one another to form the booth with a hexagonal cross-section. Each panel houses a source of radiant energy, whereby an occupant is irradiated from all sides. A base 14 supports each of the panels and serves as a floor for an occupant and incorporates certain operative functions. Roof unit 16 mates with the top of each of panels 12 and includes certain structure attendant the operation of the booth. As also shown in FIG. 4, a door 18 may be formed of two panels 12, each hinged to an adjacent panel, alternatively, two panels may be rigidly attached to one another and hinged from an adjacent panel. Handles 19 would also be employed and cooperate with suitable latches. It is to be understood that a smaller door incorporating a single panel or fractional multiples of panels may also be employed. A shroud 20 is disposed at the apex of roof unit 16 to serve as a flue for the airflow through the enclosures of panels.

Referring jointly to FIGS. 1, 2 and 3, each of panels 12 includes a shield 22 transparent to ultraviolet light of a wave length between 280 to 400 nanometers. The shield, in combination with the side and rear walls of the panel, encloses fluorescent lights serving as a source of radiant energy in each panel and protects the occupant against heat and the physical danger from broken glass should a light shatter. Floor 24 of the booth is of highly polished aluminum or similar material to reflect emitted radiant energy upwardly. Roof unit 16 also includes a source of radiant energy to irradiate an occupant of the booth from above. Thereby, the occupant is exposed to the radiant energy from all sides for an essentially even and uniform irradiation of his skin.

The source of radiant energy in each panel 12 generates a substantial amount of heat. The occupant is shielded to some extent from this heat by shields 22. However, the presently available energy sources do not operate well if the "cold spot" exceeds an ambient temperature greater than 105° F.; accordingly, means may be provided in either base 14 or roof unit 16 to blow or draw cooling air or other medium across the source of radiant energy. To maintain the occupant at a comfortable temperature, a separate cooling air flow is forced into or drawn from the compartment for the occupant, which enclosure is primarily defined by the shields.

The source of radiant energy mounted within panels 12 will be described with joint reference to FIGS. 1, 2 and 3. Each of panels 12 includes an exterior wall 26, end walls 28 and 30 and shield 22 which, in combination define an enclosure 32. As particularly shown in FIG. 3, end walls 28 and 30 are set at an angle of 60 degrees with respect to exterior wall 26 to provide angular mating of joined panels. The source of radiant energy within each panel is formed of a plurality of vertically oriented fluorescent lights arranged in two offset and overlapping rows. This arrangement provides an increase in intensity of radiant energy emitted over a single row by a factor of approximately one and one third (1⅓) without any additional expense of rear reflectors. However, a further advantage may be obtained by coating the interior surface of exterior wall 26 with a radiant energy reflective coating or a reflector 34.

As particularly illustrated in FIGS. 2 and 3, a plurality of fluorescent lights serving as radiant energy sources 36 are mounted within roof unit 16 in two stacked and overlapping rows. Again, the maximum intensity of emitted radiant energy is thereby obtained. A shield 38 transmissive to the source of radiant energy is located beneath the source of radiant energy to protect the occupant against heat and physical danger from broken glass should a light shatter. Shields 22 and 38 may be acrylic plastic of the type manufactured by Rohm and Haas of Philadelphia, PA and identified as Plexiglass II UVT sheet.

To obtain the best ratio possible of a mixture of A and B wave lengths of radiant energy, a single six foot long fluorescent light 40 emitting radiant energy of B wave length (280 to 320 nanometers) is employed per booth. An example of such a light is one manufactured by the Westinghouse Company and identified by the designation of FS-40. The remainder of the fluorescent lights 42 and including lights 36 in the ceiling emit radiant energy of A wave length (320 to 400 nanometers). An example of such a light is one manufactured by the General Electric Company and identified by the designation F72T12/BL/S1500. Because of physical limitations, the preferred ratio of 1000 to 1 cannot be accommodated in a practical commercial sized booth for a single occupant; however, the use of a single B wave length light 40 in conjunction with all of the remaining sources of radiant energy being A wave length lights 42 comes close to the optimum ratio, as a practical matter. By careful selection of shield 22 and shield 38, attenuation of the emitted desired radiant energy will be minimized.

To maximize irradiation of an occupant, the panel wall surface above the sources of radiant energy may be of reflective material 39. Similarly, those parts of the ceiling surface not otherwise occupied may also be covered with a reflective material 41.

Because the walls of enclosure 32 are sealed, a vertical flow of air therethrough can serve as a cooling medium to preclude a temperature rise of the cold spots of lights 40 and 42 to or above 105° F., the temperature below which they should be operated. As shown in FIG. 5, a baffle 44 serves as a support for a plurality of lower mountings 46, each of which supports one of lights 40 and 42. A plurality of apertures 48 are interleaved with the mountings to maximize the size of the air flow area through baffle 44. A second baffle 50 serves as a support for a plurality of upper mountings 56, each of which supports one of lights 40 and 42. A plurality of apertures 54 are also formed in this baffle to channel exhaust air from within enclosure 32. From the above description, it may be appreciated that the apertures provide air flow about each individual light and tends to provide maximum cooling thereof to prevent a temperature rise of the cold spot above 105° F.; it is of course to be understood that the air flow rate, ambient temperature and heat generation must all be taken into consideration in determining optimum parameters.

Cooling air for each of enclosures 32 flows into each of panels 12 through ventilation holes 56 in base 14 into a plenum 58. The plenum is in fluid communication with enclosure 32 through apertures 48 in baffle 44. The air flow into each of doors 18 is directly through apertures 48 formed in baffle 44, which baffle is the bottom of the door. As shown in FIG. 4, the bottom of the door is offset and above base 14. The air exhausts from enclosure 32 in the panels and doors through apertures 54 in baffle 50 into a plenum 60.

Plenum 60 is in fluid communication with chamber 62 extending within and across roof unit 16 through holes 64. The air is drawn from chamber 62 through shroud 20 by an exhaust fan 66. The air flow described above is depicted by the arrows shown in FIG. 2. The air flow rate may be regulated by temperature sensors mounted within one or more of enclosures 32.

The air flow in chamber 62 flows in and about lights 36 supported at opposed ends by mountings 68 disposed in each of supports 70 (See FIG. 6).

The cooling air for the occupant of booth 10 is introduced from a source 72 of refrigerated air into a plenum 74 within base 14 through conduit 76. The air flow from plenum 74 is introduced interior of the booth through vents 78 disposed about the perimeter of floor 24 (see also FIG. 3). Thereby, a flow of cooling air surrounds the occupant to maintain the environment within the booth at a comfortable temperature and humidity. It is to be understood that temperature and humidity regulating devices may be employed to maintain the air flowing around and about the occupant at a preset temperature and humidity.

Roof unit 16 includes a false ceiling 80 having a plurality of flues 82 through which the air from within the booth is exhausted through the roof unit into the surrounding air.

While the above detailed description of the first cooling means attendant the enclosures and the second cooling means attendant the occupant will work adequately, ambient conditions, costs or other factors may suggest different structures and flow paths. For massive air movement through the enclosures, the first cooling means may include an inlet fan of sufficient flow rate mounted in or attendant plenum 58 to force air through the enclosures. The second cooling means for the occupant may include a closed air refrigeration system. In example, duct work channeling the air from flues 82 back to the refrigeration unit could be employed; a reverse flow path could also be used.

For additional comfort of an occupant during each suntanning session within booth 10, a loud speaker 84 may be mounted in ceiling 80 for piped in music or other soothing and relaxing sounds.

A vertical hand rail 89 may be disposed adjacent one of the interior corners to aid in preventing the occupant from losing his balance during entry and departure and while he is undergoing irradiation.

While the principles of the invention have now been made clear in an illustrative embodiment, there will be immediately obvious to those skilled in the art many modifications of structure, arrangement, proportions, elements, materials, and components, used in the practice of the invention which are particularly adapted for specific environments and operating requirements without departing from those principles.

I claim:

1. A suntanning booth, said booth comprising in combination:
    (a) a compartment for defining the space for an occupant;
    (b) at least one enclosure adjacent said compartment, each said enclosure including means for inhibiting an interchange of air flow with said compartment;
    (c) said inhibiting means including a shield transmissive to radiant energy of UVA and UVB wave lengths for defining a common side of said compartment and each of said enclosures;
    (d) a selected number of sources of UVA wave length radiant energy disposed in each of said enclosures;
    (e) a selected number of sources of UVB wave length radiant energy disposed in each of said enclosures;
    (f) first means for cooling said compartment with a first flow of air; and
    (g) second means for cooling each of said enclosures with a second flow of air, the path of said second flow of air through each of said enclosures being segregated from the path of said first flow of air by at least said inhibiting means.

2. The booth as set forth in claim 1 wherein said UVA wave length and UVB wave length sources of radiant energy comprise a plurality of flourescent lights, selected ones of which emit A wave length radiant energy and selected ones of which emit B wave length radiant energy.

3. The booth as set forth in claim 2 wherein selected ones of said fluorescent lights are mounted in each of said enclosures in a stacked and overlapping relationship to one another.

4. The booth as set forth in claim 2 wherein selected ones of said fluorescent lights are mounted in each of said enclosures in two adjacent rows, said fluorescent lights of one of said rows being offset from said fluorescent lights of the other of said rows to maximize the density of the emitted radiant energy.

5. The booth as set forth in claim 4 including a reflective surface located behind said rows.

6. The booth as set forth in claim 1 wherein said UVB wave length source comprises one of a first type of fluorescent lights disposed in one of said enclosures and wherein said UVA wave length source comprises a plurality of a second type of fluorescent lights disposed in each of said enclosures.

7. The booth as set forth in claim 6 wherein said first type comprises a fluorescent light manufactured by the Westinghouse Company and identified by the designation FS-40 and said second type comprises a fluorescent light manufactured by the General Electric Company and identified by the designation F72T12/BL/S1500.

8. The booth as set forth in claim 1 wherein a sufficient number of said enclosures are employed to surround the occupant and irradiate the occupant from all sides.

9. The booth as set forth in claim 8 including a further source of radiant energy disposed overhead of the occupant for irradiating the occupant from above.

10. The booth as set forth in claim 9 including a radiant energy reflective floor under the occupant for irradiating the occupant from below with reflected radiant energy.

11. The booth as set forth in claim 1 wherein each of said shields comprises sheet material manufactured by the Rohm and Haas Company and identified by the designation Plexiglas II UVT.

12. The booth as set forth in claim 1 including means for altering the ratio of UVA and UVB wave length radiant energy within each of said enclosures.

* * * * *